(12) United States Patent
Kitano

(10) Patent No.: US 8,657,738 B2
(45) Date of Patent: Feb. 25, 2014

(54) ENDOSCOPE SYSTEM AND ILLUMINATION LIGHT CONTROL METHOD THEREFOR

(75) Inventor: Ryou Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 130 days.

(21) Appl. No.: 13/361,331

(22) Filed: Jan. 30, 2012

(65) Prior Publication Data

US 2012/0245421 A1    Sep. 27, 2012

(30) Foreign Application Priority Data

Mar. 22, 2011    (JP) ................................. 2011-062156

(51) Int. Cl.
*A61B 1/06*    (2006.01)
(52) U.S. Cl.
USPC .......................................... 600/168; 600/182
(58) Field of Classification Search
USPC ................. 600/103, 129, 160, 167–168, 173, 600/176–178, 181–182
See application file for complete search history.

(56) References Cited

U.S. PATENT DOCUMENTS

| | | | | |
|---|---|---|---|---|
| 2001/0044571 A1* | 11/2001 | Mitsumori | .................... | 600/167 |
| 2004/0097791 A1* | 5/2004 | Tokuda et al. | ................ | 600/173 |
| 2006/0084841 A1* | 4/2006 | Minami | ........................ | 600/168 |
| 2008/0177144 A1* | 7/2008 | Otawara | ........................ | 600/157 |
| 2008/0262315 A1* | 10/2008 | Inoue | ............................. | 600/168 |
| 2010/0137682 A1* | 6/2010 | Doguchi et al. | .............. | 600/109 |

FOREIGN PATENT DOCUMENTS

JP    9-66020 A    3/1997

* cited by examiner

*Primary Examiner* — Philip R Smith
(74) *Attorney, Agent, or Firm* — Birch, Stewart, Kolasch & Birch, LLP

(57) ABSTRACT

In an endoscope system, a light guide for conducting illumination light from a light source to an endoscope distal end consists of a first fiber bundle and a second fiber bundle. Optical fibers of the first fiber bundle have a smaller numerical aperture than optical fibers of the second fiber bundle. A light volume control mechanism is controlled to project the illumination light only from the first fiber bundle in a close-up inspection mode. In an ordinary inspection mode, the illumination light is projected only from the second fiber bundle. When the volume of light projected from the second fiber bundle toward a target site is insufficient in the ordinary inspection mode, the light volume control mechanism is controlled to let the illumination light be projected from the first fiber bundle.

10 Claims, 7 Drawing Sheets

ENDOSCOPE SYSTEM AND ILLUMINATION LIGHT CONTROL METHOD THEREFOR

BACKGROUND OF THE INVENTION

1. Field of the Invention

The present invention relates to an endoscope system, in which a light guide conducts light for illuminating a subject under inspection from a light source toward the subject, and a method of controlling illumination light for the endoscope system.

2. Description of the Related Art

In the medical field, endoscopes are frequently used to acquire images of internal sites of test subjects for the purpose of diagnoses or surgeries. These endoscopes mostly use an image sensor that captures images of the subject through an inspection window at a distal end of a probing portion that may be inserted into the subject body. The endoscopic images acquired through the image sensor are displayed on a monitor. Many of recent endoscopes have a function to change the image magnification by changing the focal length of an imaging lens system that is located between the inspection window and the image sensor. The image magnification increases with increasing focal length, zooming in the target site and enlarging the image magnification on the monitor.

With this type of zoomable endoscope, the diagnostic inspection is generally done first in an ordinary inspection mode at a low image magnification (short focal length), to make the screening to search for and locate a suspected site of lesions. Thereafter the focal length is set longer or moved to the telephoto side and, at the same time, the distal end of the endoscope containing the imaging lens system is set closer to the located site for macro imaging or close-up inspection to inspect the target site in the enlarged view.

Such close-up inspection allows checking the condition of the target site in more detail. Especially, the condition of superficial blood vessels, such as presence of any heteromorphic vessels, is an important factor for diagnosis and follow-up examination. In order to facilitate inspection of superficial blood vessels and improve the accuracy of diagnosis, it is known using such illumination light that contains a large fraction of blue light component with shorter wavelengths. This is because hemoglobin contained in blood shows high absorbance to the blue light component. Also because light components of longer wavelengths will reach the deeper layer of the target site, if the illumination light contains a lot of long-wavelength components, the deeper layer will be illuminated so much that the contrast of the superficial blood vessels to other tissues and organs will be lowered undesirably.

In the endoscope system, the illumination light is usually transmitted from a light source through a light guide to the distal end of the probing portion and projected toward the target site. The light guide is made of a bundle of optical fibers. Due to the properties of the optical fibers, light transmitted through the light guide will attenuate with the length of the light guide. Particularly, light components of shorter wavelengths tend to have greater attenuation rates.

JPA 1997-66020 discloses an endoscope that uses two kinds of light guides; one uses optical fibers with a large aperture size and the other uses optical fibers with a small aperture size. In this known endoscope, the light guide consisting of large aperture optical fibers is used for wide-angle luminous intensity distribution of the illumination light, whereas the light guide consisting of small aperture optical fibers is used for narrow-angle luminous intensity distribution of the illumination light. Since fluxes of wide distribution and fluxes of narrow distribution are respectively emitted from these light guides, a single element projection lens may be used for either kind of light guide without the need for any complicated illumination lens system. In this prior art, the intensity of the narrow distribution fluxes may be increased to illuminate deeper into a tubular site, or the intensity of the narrow distribution fluxes may be lowered to obtain illumination light of wide and flat luminous intensity distribution, which is suitable for inspection of a planer site.

Large aperture optical fibers are advantageous in order to obtain a large light volume because the large aperture optical fibers let the illumination light from the light source enter at a high efficiency. However, because the light will reflect so much inside the large aperture optical fiber and the refraction factor of the large aperture optical fiber is high, the blue light component will attenuate drastically while the illumination light is being transmitted through the large aperture optical fibers. Therefore, illumination light will little contain the blue light component as projected from the large numerical aperture optical fibers, and is unsuitable for inspection of superficial blood vessels. By contrast, the light guide consisting of small numerical aperture optical fibers tends to reduce the volume of light so much that this type light guide is unsuitable for the ordinary inspection. In order to obtain a sufficient volume of illumination light, a high power light source is necessary, which is disadvantageous in view of space efficiency.

SUMMARY OF THE INVENTION

In view of the foregoing, an object of the present invention is to provide an endoscope system and a method of controlling illumination light for the endoscope system, whereby illumination light of a sufficient volume for the ordinary inspection as well as illumination light optimum for the close-up inspection can easily be obtained.

According to the present invention, an endoscope system using an imaging device having a varifocal imaging optical system comprises:

a light guide for conducting illumination light from a light source to a distal end of an endoscope to project the illumination light toward a target site, the light guide comprising a first fiber bundle consisting of optical fibers of a first numerical aperture and a second fiber bundle consisting of optical fibers of a second numerical aperture larger than the first numerical aperture, the first and second light bundles having respective inlet ends for entry of the illumination light from the light source and respective outlet ends placed in the distal end of the endoscope;

a light volume control mechanism switchable between a second fiber bundle unblocking position allowing the illumination light from the light source to enter the second fiber bundle and a second fiber bundle blocking position blocking the illumination light from entering the second fiber bundle; and a control device for controlling the light volume control mechanism, the control device setting the light volume control mechanism in the second fiber bundle blocking position in a close-up inspection mode, wherein the imaging optical system has a focal length equal to or longer than a predetermined value, to project the illumination light only from the first fiber bundle in the close-up inspection mode.

The first and second fiber bundles may preferably be configured such that the illumination light projected from the first fiber bundle has a smaller volume than the illumination light projected from the second fiber bundle while the light volume control mechanism is in the second fiber bundle unblocking position. In one embodiment, the first fiber bundle consists of a smaller number of optical fibers than the second fiber bundle.

In an end face of the distal end, an inspection window for capturing images through the imaging device, a first lighting window for projecting the illumination light from the first fiber bundle, and a second lighting window for projecting the illumination light from the second fiber bundle may preferably be provided such that the first lighting window is located closer to the inspection window than the second lighting window to the inspection window.

Preferably, the inlet ends of the first and second fiber bundles are united together and partitioned into respective zones, while the outlet ends of the first and second fiber bundles constitute two branches of the light guide.

Preferably, the first numerical aperture is less than 0.5, and the second numerical aperture is not less than 0.5.

In an ordinary inspection mode, wherein the imaging optical system has a focal length shorter than the predetermined value, the control device may preferably set the light volume control mechanism in the second fiber bundle unblocking position to project the illumination light from the second fiber bundle toward the target site in the ordinary inspection mode.

In a preferred embodiment, the light volume control mechanism is switchable between a first fiber bundle unblocking position allowing the illumination light from the light source to enter the first fiber bundle and a first fiber bundle blocking position blocking the illumination light from entering the first fiber bundle. In this embodiment, the control device may preferably set the light volume control mechanism in the first fiber bundle blocking position in the ordinary inspection mode.

In one embodiment, the light volume control mechanism may individually adjust the volume of light entering the first fiber bundle from the light source and the volume of light entering the second fiber bundle from the light source. In the close-up inspection mode, the control device may preferably control the light volume control mechanism to keep the second fiber bundle blocking position and adjust the volume of light entering the first fiber bundle when the volume of light projected toward the target site is excessive or insufficient. In the ordinary inspection mode, the control device may also control the light volume control mechanism to keep the first fiber bundle blocking position and adjust the volume of light entering the second fiber bundle when the volume of light projected toward the target site is excessive, or retreat from the first fiber bundle blocking position to adjust the volume of light entering the first fiber bundle when the volume of light projected only from the second fiber bundle is insufficient.

According to another aspect of the present invention, a method of controlling illumination light of an endoscope system having a varifocal imaging optical system comprises the steps of:

determining whether the endoscope system is in a close-up inspection mode, wherein the imaging optical system has a focal length equal to or longer than a predetermined value, or an ordinary inspection mode, wherein the imaging optical system has a focal length shorter than the predetermined value; and controlling the entry of illumination light from a light source into a light guide for conducting the illumination light from the light source to an endoscope distal end to project the illumination light toward a target site, the light guide comprising a first fiber bundle consisting of optical fibers of a first numerical aperture and a second fiber bundle consisting of optical fibers of a second numerical aperture larger than the first numerical aperture, such that the illumination light from the light source enters only the first fiber bundle in the close-up inspection mode.

Preferably, when the volume of light projected toward the target site is excessive or insufficient in the close-up inspection mode, the volume of light entering the first fiber bundle is adjusted while keeping blocking the illumination light from entering the second fiber bundle.

In the ordinary inspection mode, the entry of the illumination light from the light source may preferably be controlled such that the illumination light from the light source enters only the second fiber bundle.

When the volume of light projected toward the target site is excessive or insufficient in the ordinary inspection mode, the volume of light entering the second fiber bundle may preferably be adjusted while keeping blocking the illumination light from entering the first fiber bundle.

When the volume of illumination light projected only from the second fiber bundle is insufficient in the ordinary inspection mode, the illumination light from the light source may preferably be allowed to enter the first fiber bundle while adjusting the volume of light entering the first fiber bundle.

According to the present invention, the target site is illuminated only with the illumination light from the first fiber bundle having a small numerical aperture in the close-up inspection mode where the focal length of the imaging optical system is not less than a predetermined value. The illumination light from the first fiber bundle having the small numerical aperture contains blue light component so much that it is especially suitable for the close-up inspection of superficial blood vessels. On the other hand, in the ordinary inspection mode where the focal length is less than the predetermined value, the illumination light may be projected through the second fiber bundle having a large numerical aperture. Thus the illumination light can get a sufficient volume in the ordinary inspection mode.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
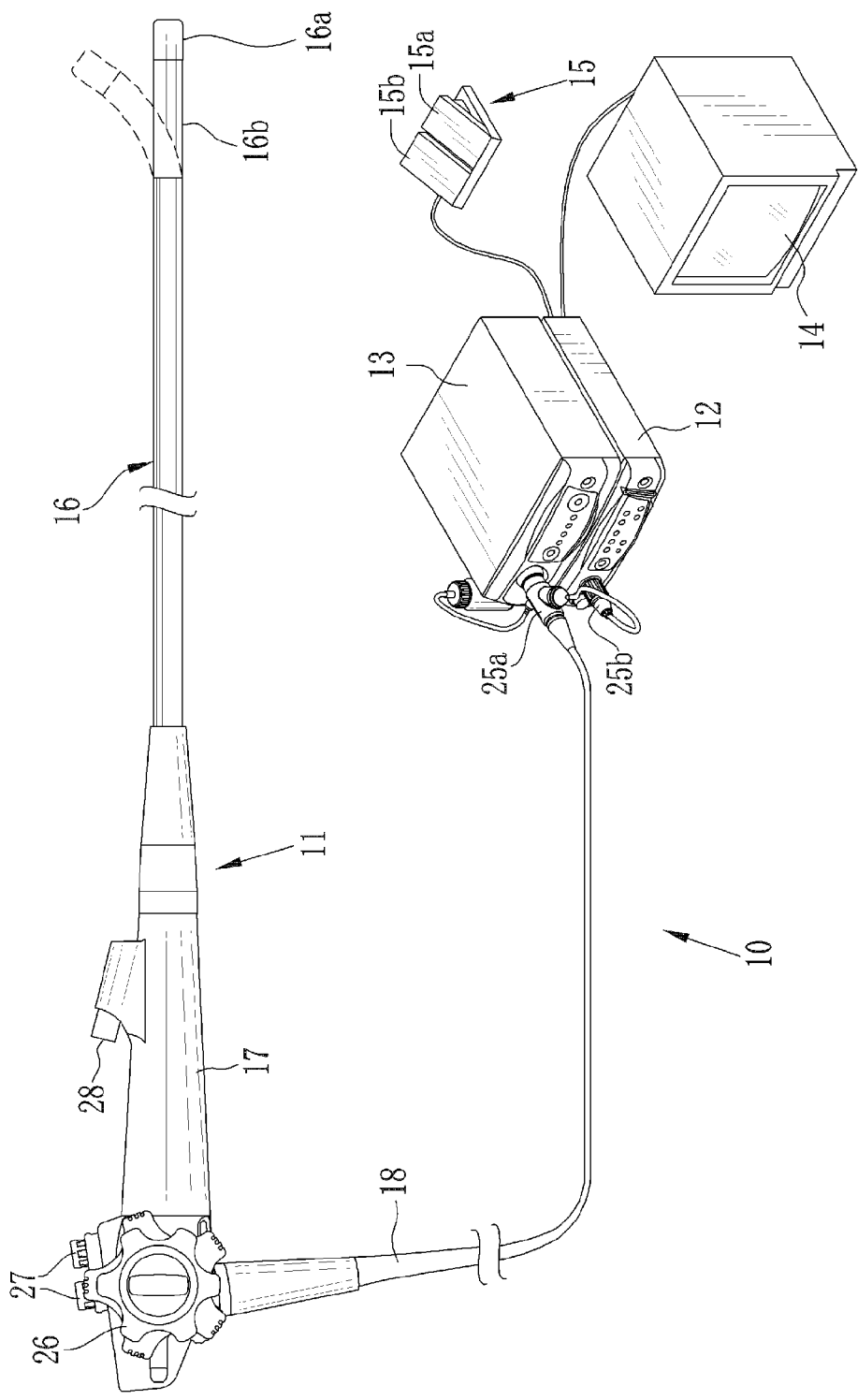
FIG. 1 is a schematic diagram illustrating an endoscope system.

As shown in FIG. 1, an endoscope system 10 includes an electronic endoscope 11 for acquiring image signals representative of a target site inside a patient, a processor unit 12 for producing endoscopic images of the target site from the image signals acquired by the electronic endoscope 11, a light source unit 13 having a light source for illumination light to the target site, a monitor 14 for displaying the endoscopic images, and foot pedals 15 operated to change the focal length of an imaging optical system of the endoscope 11.

The endoscope system 10 is switchable between an ordinary inspection mode and a close-up inspection mode according to the focal length of the imaging optical system. The ordinary inspection mode is for search and location of a suspected site of lesions at a low image magnification. The close-up inspection mode is for close-up inspection of the target site at a high image magnification, especially for inspection of superficial blood vessels.

The electronic endoscope 11 has a flexible probing portion 16 insertable into the subject body, a handling portion 17 coupled to a proximal end of the probing portion 16 for gripping the electronic endoscope 11 and handling the probing portion 16, a universal cord 18 connecting the handling portion 17 to the processor unit 12 and the light source unit 13. In a distal end of the probing portion 16, the endoscope distal end 16a, optical systems for illuminating the target site, and the imaging optical system and an image sensor for acquiring images of the target site are incorporated. A proximal end of the scope distal end 16a is coupled to a curving portion 16b that can curve to steer the scope distal end 16a in any direction.

Figure 2:
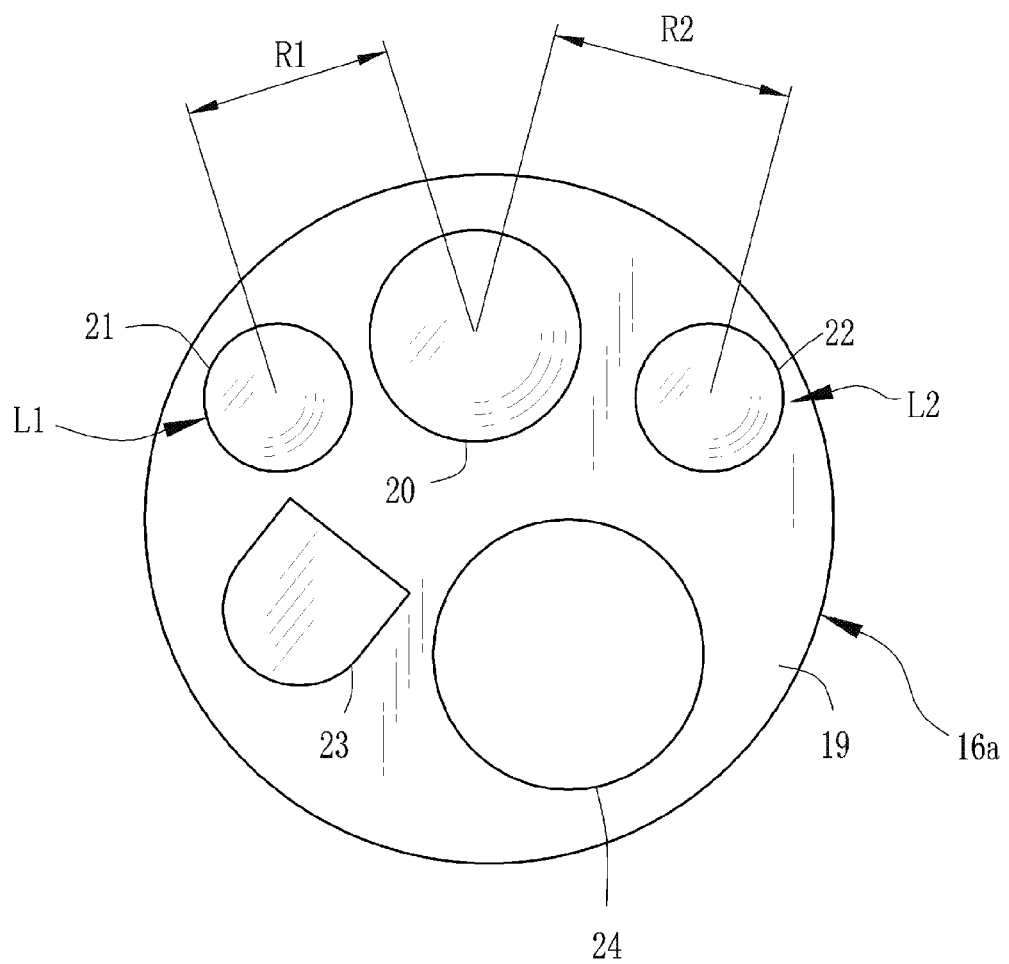
FIG. 2 is an explanatory diagram illustrating an end face of a distal end of an electronic endoscope.

As shown in FIG. 2, in an end face 19 of the scope distal end 16a, an inspection window 20, there are formed a first lighting window 21a of a first illumination system L1, a second lighting window 22 of a second illumination system L2, an insufflating and watering nozzle 23, a tool outlet 24 as an exit of the tool channel that is formed along inside the probing portion 16.

The first illumination system L1 is mainly for use in the close-up inspection mode where the end face 19 is moved closer to the target site, and illumination light is projected through the first lighting window 21 toward the target site to be imaged through the inspection window 20. The second illumination system L2 is used in the ordinary inspection mode, wherein the illumination light is projected through the second lighting window 22 toward the target site while the end face 19 is placed distant from the target side in comparison with the close-up inspection mode. In either mode, in order to match the lighting field of the illumination light with the imaging field, the first lighting window 21 is disposed closer to the inspection window 20 as compared to the second lighting window 22. That is, the distance R1 of the first lighting window 21 to the inspection window 20 is shorter than the distance R2 of the second lighting window 22 to the inspection window 20. Note that an optical axis of the first illumination system L1 may be inclined so as to match the lighting field of the first illumination system L1 with the imaging field.

Referring back to FIG. 1, the handling portion 17 is provided with an angle knob 26, operation buttons 27, a tool inlet 28, etc. The angle knob 26 is turned to control the direction and amount of curvature of the probing portion 16. The operation buttons 27 are operated for insufflation (air-supply), watering, suction, or other procedures. The tool inlet 28 leads to a tool channel. Into the universal cord 18, an insufflating and watering channel, signal cables, and a light guide 30 (see FIG. 3) are incorporated.

The foot pedals 15 have a pair of pedals 15a and 15b. For example, the pedal 15a is operated to increase the focal length of the imaging optical system, zooming toward the telephoto terminal. On the other hand, the pedal 15b is operated to decrease the focal length of the imaging optical system, zooming toward the wide-angle terminal.

Figure 3:
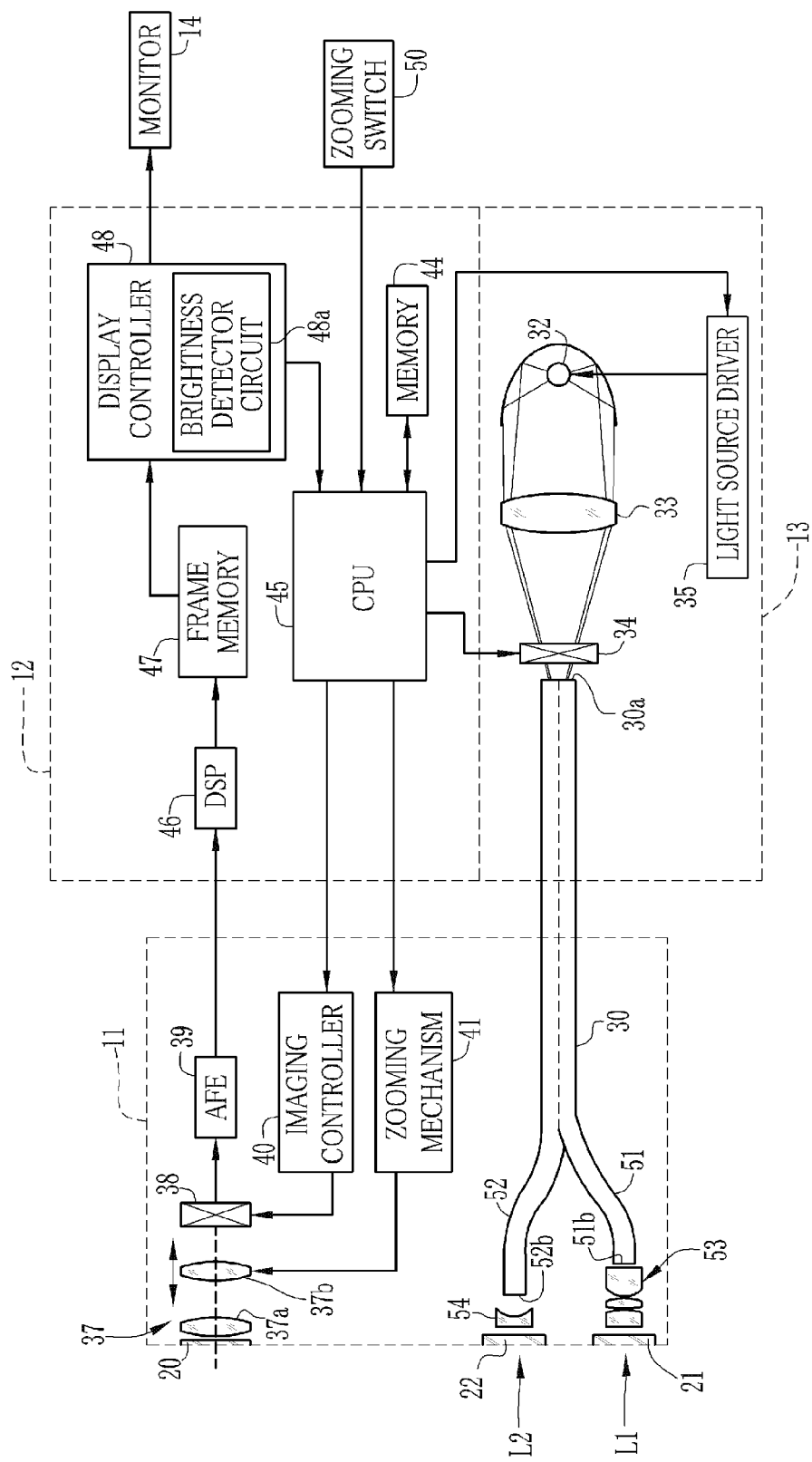
FIG. 3 is a block diagram illustrating an internal structure of the endoscope system.

As shown in FIG. 3, the light source unit 13 is provided with a light source 32, a condenser lens 33, a light volume control mechanism 34, and a light source driver 35. The light source 32 is configured to generate white illumination light that includes spectral components of a wavelength range absorbable to hemoglobin, i.e. blue light component. For example, the light source unit 13 may be a xenon lamp or a white LED, which may generate white illumination light covering a broad wavelength band ranging from red to blue (about 470 to 700 nm).

The condenser lens 33 condenses the illumination light from the light source 32 to gather beams into an inlet port 30a of the light guide 30. The light volume control mechanism 34 is disposed in between the condenser lens 33 and the inlet port 30a, in order to control the light volume of illumination light entering the inlet port 30a. The light volume control mechanism 34 is controlled by the control of the processor unit 12, as will be described in detail later. The light source driver 35 actuates the light source 32 under the control of the processor unit 12.

The electronic endoscope 11 includes the light guide 30, an imaging optical system 37, an image sensor 38, an analog front end (AFE) 39, an imaging controller 40, and a zooming mechanism 41. The imaging optical system 37 and the image sensor 38 constitute an imaging device. The imaging optical system 37, which is composed of an objective lens 37a, a zoom lens 37b and other components, is a zoom lens system or varifocal lens system that may change the focal length. The objective lens 37a is exposed through the inspection window 20.

The zoom lens 37b is movable in its axial direction between one terminal position corresponding to the telephoto terminal providing the longest focal length and the other terminal position corresponding to a wide-angle terminal providing the shortest focal length. The zoom lens 37b is moved in the axial direction by a zooming mechanism 41, which is driven under the control of the processor unit 12, to change the image magnification (the magnification of the displayed image).

The image sensor 38 may for example be a CCD image sensor. The image sensor 38 converts an optical image formed through the imaging optical system 37 into electric image signal, and output it to the AFE 39. The image sensor 38 may as well be of an MOS type, instead of the CCD type. The image sensor 38 outputs the image signal to the AFE 39 at a predetermined frame rate on the basis of a drive signal from the imaging controller 40 under the control of the processor unit 12.

The AFE 39 consists of a correlated double-sample circuit (CDS), an automatic gain control circuit (AGC), and an analog-to-digital converter (A/D). The CDS renders the image signal from the image sensor 35 with correlated double-sampling to reduce noises from the image signal. The AGC amplifies the image signal after the noise reduction through the CDS. The A/D converts the amplified image signal to digital image data of a predetermined bit number, and sends the image data to the processor unit 12.

The processor unit 12 includes a memory 44, a CPU 45, a digital signal processor (DSP) 46, a frame memory 47, and a display controller 48. The memory 44 stores various programs and data for controlling the endoscope system 10. On the basis of the programs and data read out from the memory 44, the CPU 45 controls respective components of the processor unit 12, the light volume control mechanism 34 of the light source unit 13, and the light source driver 35.

The DSP 46 processes the image data from the AFE 39 for image-rendering, such as white balance control, color control, gradation control, and sharpness control. The processed image data are stored in the frame memory 47. The display controller 48 reads out the image data from the frame memory 47, to drive the monitor 14 based on the image data. Thus, the image of the subject captured through the image sensor 38 is displayed as an endoscopic image on the monitor 14. The display controller 48 also includes a luminance detection circuit 48a for detecting luminance of the endoscopic image from the image data. Information on the detected luminance is fed to the CPU 45 for use in controlling the volume of illumination light.

The zoom switch 50 is incorporated into the foot pedals 15, to generate zooming signals in response to the operation on the pedal 15a or 15b. According to the zooming signal, the CPU 45 drives the zooming mechanism 41 to move the zoom lens 37b. Thus, the image magnification changes according to the zooming operation on the foot pedals 15. Alternatively, the zoom switch 50 may be provided in the handling portion 17 of the electronic endoscope 11.

In one embodiment, the CPU 45 operates in the close-up inspection mode when the focal length of the imaging optical system 37 is not less than a predetermined value, e.g. a middle focal length between the wide-angle terminal and the telephoto terminal. When the focal length is less than the predetermined value, the CPU 45 operates in the ordinary inspection mode. Switching between the ordinary inspection mode and the close-up inspection mode may be done depending on the focal length in other various ways.

For example, a value that is on the telephoto side of the middle focal length point may be used as a threshold for switching between the ordinary inspection mode and the close-up inspection mode. In that case, the ordinary inspection mode may be taken when the focal length is on the wide-angle terminal side of the threshold value, and the close-up inspection mode may be taken when the focal length is on the telephoto side. In a case where the focal length is just switchable between the wide-angle terminal and the telephoto terminal, the ordinary inspection mode may be taken at the wide-angle terminal, and the close-up inspection mode may be taken at the telephoto terminal.

The light guide 30 includes a first fiber bundle 51 and a second fiber bundle 52. These fiber bundles 51 and 52 are united together to form a single inlet port 30a on the side of the light source unit 13. The light guide 30 is conducted as a united string through along the probing portion 16 and forks into two branches for example at the scope distal end 16a. In the illustrated embodiment, the first fiber bundle 51 and the second fiber bundle 52 form the single inlet port 30a so that they may share the same light source and the same condenser lens. However, it is possible to separate the first fiber bundle 51 and the second fiber bundle 52 through the whole length.

The first fiber bundle 51 consists of a lot of optical fibers with a small numerical aperture. The second fiber bundle 52 consists of a lot of optical fibers with a large numerical aperture. That is, the numerical aperture (NA2) of the optical fibers of the second fiber bundle 52 is larger than the numerical aperture (NA1) of the optical fibers of the first fiber bundle 51 (NA1<NA2). The numerical aperture of the first fiber bundle 51 is preferably less than 0.5, while the numerical aperture of the second fiber bundle 52 is preferably not less than 0.5.

The first lighting lens 53 is placed behind the first lighting window 21. The first lighting lens 53 and the first fiber bundle 51 constitute the first illumination system L1. The second lighting lens 54 is placed behind the second lighting window 22. The second lighting lens 54 and the second fiber bundle 52 constitute the second illumination system L2.

Because the first illumination system L1 is used in the close-up inspection mode where the scope distal end 16a is set close to the target site, the light volume from the first illumination system L1 may be lower than that from the second illumination system L2, which is used in the ordinary inspection mode. For this reason, the light volume from the first illumination system L1 is set lower than that from the second illumination system L2, for example, by reducing the number of optical fibers of the first fiber bundle 51 as compared to the number of optical fibers of the second fiber bundle 52.

The illumination light projected from an outlet 51b of the first fiber bundle 51 enters the first lighting lens 53. The first lighting lens 53 is configured to distribute the illumination light from the outlet 51b across a wider range for illuminating the imaging field as wide and flat as possible in the close-up inspection mode where the outlet 51b is set close to the target site. On the other hand, the illumination light projected from the outlet port 52b of the second fiber bundle 52 enters the second lighting lens 54. The second lighting lens 54 is configured to distribute the illumination light from the outlet port 52b across a narrower range in the ordinary inspection mode in comparison with the first lighting lens 53.

Figure 4:
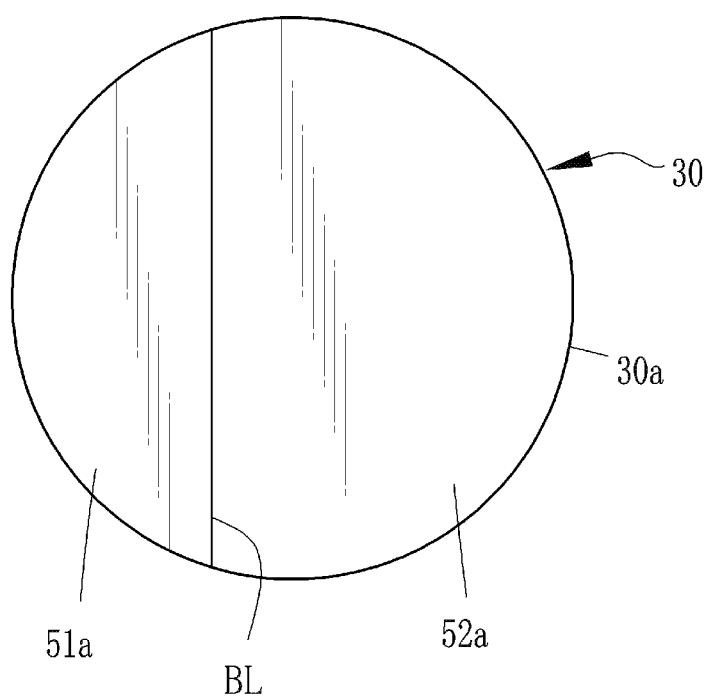
FIG. 4 is an explanatory diagram illustrating an end face of an inlet port of a light guide.

As shown in FIG. 4, the inlet port 30a of the light guide 30 is divided by a straight-linear border BL into a first entrance zone 51a for the first fiber bundle 51 and a second entrance zone 52a for the second fiber bundle 52. The optical fibers of the first fiber bundle 51 are placed in the first entrance zone, while the optical fibers of the second fiber bundle 52 are placed in the second entrance zone 52a.

The illumination light entering the first entrance zone 51a travels through the first fiber bundle 51 and emits from the outlet 51b to the first lighting lens 53. The illumination light entering the second entrance zone 52a travels through the second fiber bundle 52 and emits from the outlet 52b to the second lighting lens 54. Thus the illumination light from the first fiber bundle 51 is projected through the first lighting lens 53 to the target site, and the illumination light from the second fiber bundle 52 is projected through the second lighting lens 54 to the target site.

Figure 5A:
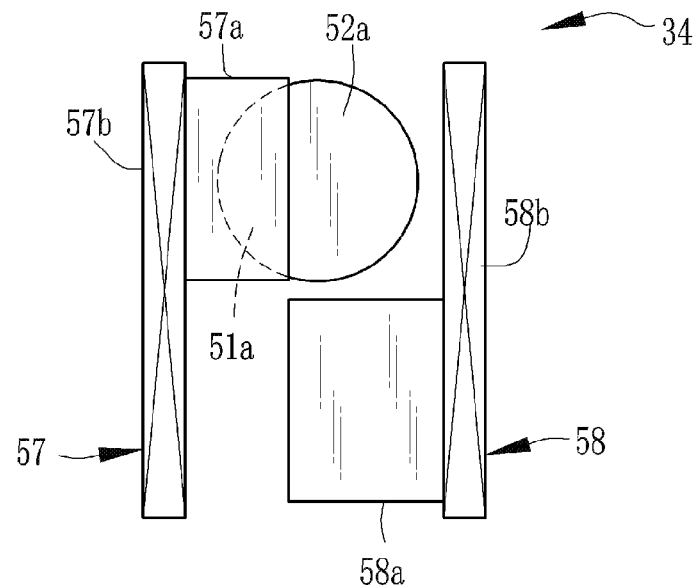
FIGS. 5A and 5B are explanatory diagrams illustrating the operation of a light volume control mechanism.
Figure 5B:
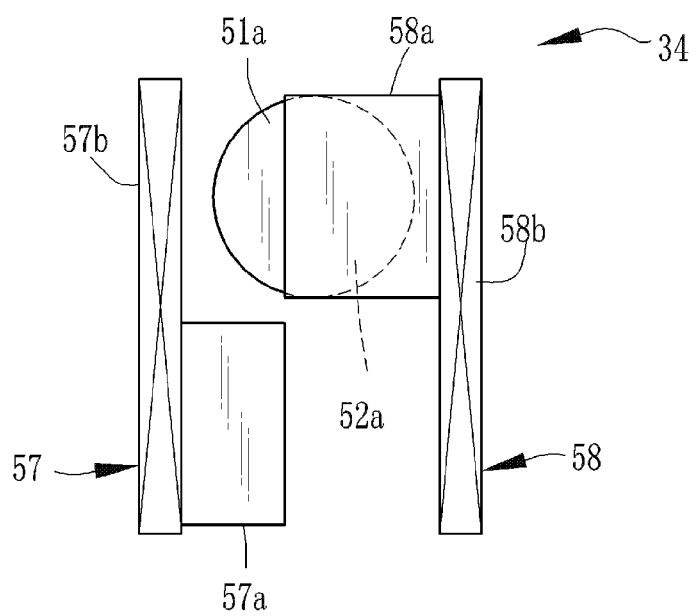

As shown in FIG. 5, the light volume control mechanism 34 consists of a first control unit 57 for controlling the light volume of the first illumination system L1 and a second control unit 58 for controlling the light volume of the second illumination system L2. The first control unit 57 includes a first light blocking blade 57a and an actuator 57b. The first light blocking blade 57a is movable into and out of an optical path of the illumination light in between the first entrance zone 51a and the condenser lens 33. The first light blocking blade 57a is movable between a blocking position (first fiber bundle blocking position) as shown in FIG. 5A, inserted in the optical path to cover up the first entrance zone 51a and block the illumination light from the first entrance zone 51a, and an unblocking position (first fiber bundle unblocking position) as shown in FIG. 5B, retreating from the optical path to allow the illumination light to incident on the whole area of the first entrance zone 51a. The actuator 57b is driven to move the first light blocking blade 57a between the blocking position and the unblocking position under the control of the CPU 45.

The second control unit 58 includes a second light blocking blade 58a and an actuator 58b. The second light blocking blade 58a is movable into and out of an optical path of the illumination light in between the second entrance zone 52a and the condenser lens 33. The second light blocking blade 58a is movable between a blocking position (second fiber bundle blocking position) as shown in FIG. 5B, inserted in the optical path to cover up the second entrance zone 52a and block the illumination light from the second entrance zone 52a, and an unblocking position (second fiber bundle unblocking position) as shown in FIG. 5A, retreating from the optical path to allow the illumination light to fall on the whole area of the second entrance zone 52a. The actuator 58b is driven to move the second light blocking blade 58a between the blocking position and the unblocking position under the control of the CPU 45.

The CPU 45 sets the second light blocking blade 58a in the blocking position in the close-up inspection mode, to illuminate the target site only with the illumination light from the first illumination system L1. Namely, the first fiber bundle 51 with small numerical aperture and hence less attenuation of blue light component is used for illumination in the close-up inspection mode. Because the second fiber bundle 52 with large numerical aperture will attenuate short-wavelength light components, including blue light component, more than long-wavelength light components of the light from the light source 32, and hence the light projected from the second fiber bundle 52 contains lots of long-wavelength light components, the second fiber bundle 52 is not used for illumination in the close-up inspection mode.

In the close-up inspection mode, the CPU 45 also controls the amount of insertion of the first light blocking blade 57a into the optical path while keeping the second light blocking blade 58a in the blocking position, to adjust the volume of illumination light from the first illumination system L1 properly according to the luminance information from the display controller 48.

In the ordinary inspection mode, the CPU 45 sets the first light blocking blade 57a at the blocking position, and controls the amount of insertion of the second light blocking blade 58a into the optical path to adjust the volume of illumination light from the second illumination system L2 according to the luminance information from the display controller 48. Moreover, if the light volume from the second illumination system L2 is insufficient, the CPU 45 displaces the first light blocking blade 57a from the blocking position toward the unblocking position till the total volume of the illumination light gets proper.

Figure 6:
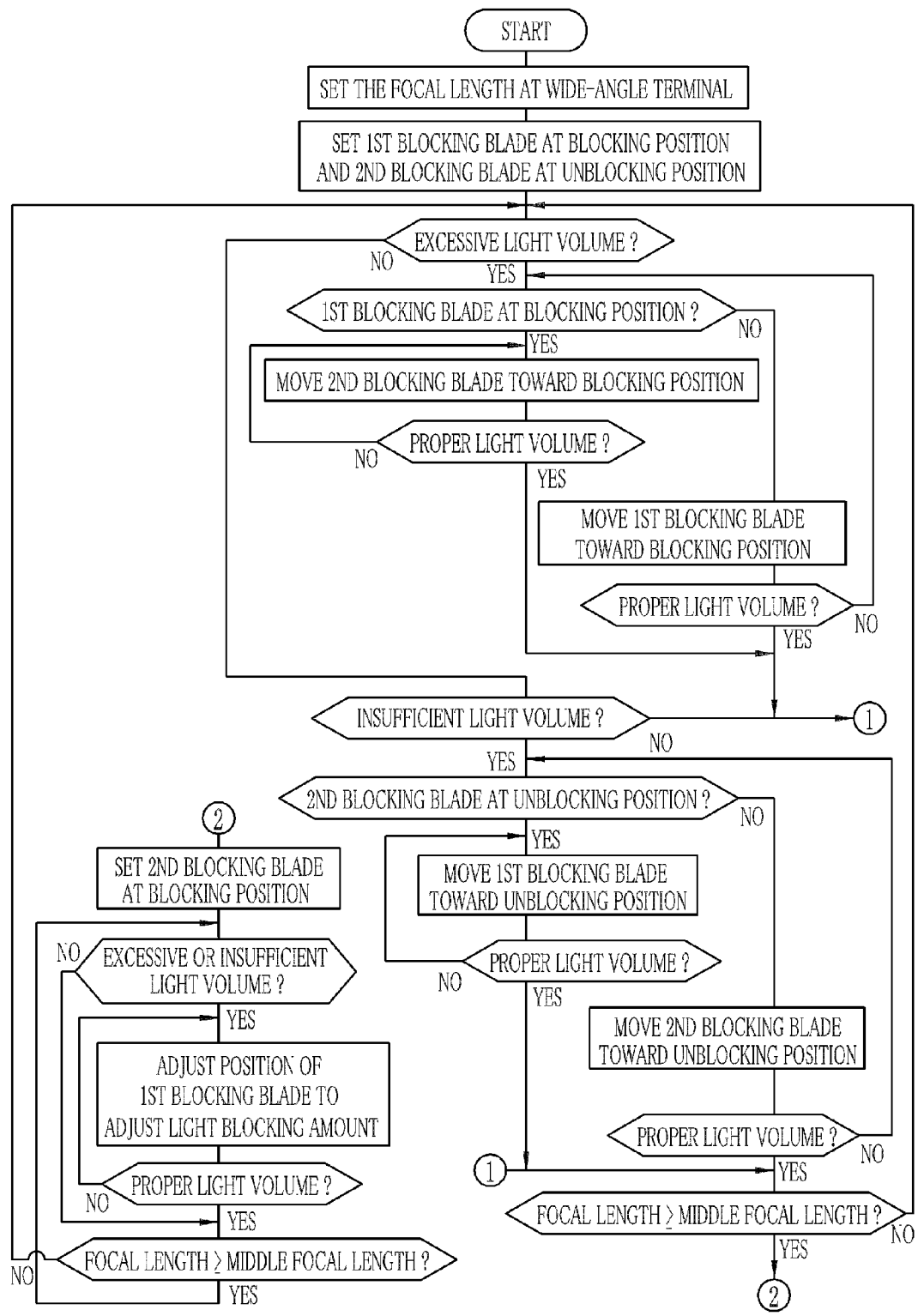
FIG. 6 is a flowchart illustrating a program sequence for controlling the operation of the light volume control mechanism.

The operation of the endoscope system 10 configured as above will be described with reference to the flowchart of FIG. 6. When the processor unit 12 and the light source unit 13 are powered on to execute a preparatory process for an endoscopic examination, the image sensor 38 is actuated, and the light source 32 is turned on. In the initial stage immediately after the power-on, the imaging optical system 37 may be set at the wide-angle terminal, and the system 10 may be set in the ordinary inspection mode. When the preparatory process is accomplished, the probing portion 16 may be inserted into the subject body.

The illumination light from the light source 32 is converged through the condenser lens 33 to the inlet port 30a of the light guide 30. In the ordinary inspection mode, the first light blocking blade 57a may initially be set at the blocking position, while the second light blocking blade 58a may be set at the unblocking position, so that the illumination light from the condenser lens 33 will fall only in the second entrance zone 52a. As a result, the illumination light is conducted through the second fiber bundle 52 to the scope distal end 16a and exits from the outlet port 52b of the second fiber bundle 52. Then, the illumination light is projected through the second lighting lens 54 and the second lighting window 22 into the subject body. The illumination light from the second illumination optical system L2 distributes across a narrow field, which is preferable to illuminate a tubular site, like esophagus, of the subject body.

The tubular site illuminated with the illumination light from the second illumination system L2 is imaged through the imaging optical system 37 and captured as electric image signal by the image sensor 38. The image signal output from the image sensor 38 is processed through the AFE 39 to acquire digital image data of the imaged site. The subsequent image data is sent to the DSP 46, which processes the image data for various image-rendering. The processed image data is stored in the frame memory 47, and is read by the display controller 48 to display an endoscopic image on the monitor 14 on the basis of the image data. Each time the image sensor 38 captures a frame of image signal at the predetermined frame rate, the frame memory 47 is rewritten with new image data, so that the tubular site may be observed as moving images on the monitor 14.

During the imaging, the display controller 48 detects luminance of the endoscopic image from the image data as read out from the frame memory 47, and feeds the information on the detected luminance to the CPU 45. Then the CPU 45 controls the volume of the illumination light based on the luminance information.

For example, when the detected luminance is so high that the CPU 45 judges that the light volume is excessive, the CPU 45 first checks whether the first light blocking blade 57a of the first control unit 57 is in the blocking position or not. If the first light blocking blade 57a is in the blocking position, the CPU 45 controls the second control unit 58 to move the second light blocking blade 58a toward the blocking position and stop it at a position where the light volume gets proper with respect to the luminance information.

If the first light blocking blade 57a is not in the blocking position, that is, when the illumination light is being projected also from the first illumination system L1, the CPU 45 controls the first control unit 57 to move the first light blocking blade 57a toward the blocking position till the light volume gets proper. If the light volume is still excessive even when the first light blocking blade 57a gets to the blocking position, the first light blocking blade 57a is held in the blocking position, and the second light blocking blade 58a is moved toward the blocking position and stopped at a position where the CPU 45 judges by the luminance information that the light volume gets proper.

On the other hand, when the luminance of the captured image is so low that the CPU 45 judges that the light volume is insufficient, the CPU 45 first checks whether the second light blocking blade 58a is in the unblocking position or not. If, for example, the second light blocking blade 58a is not in the unblocking position and hence the light volume of the illumination light from the second illumination system L2 is not at the maximum, the second light blocking blade 58a will be moved toward the unblocking position till the light volume gets proper. If the light volume is still insufficient even when the second light blocking blade 58a gets to the unblocking position, or if the second light blocking blade 58a is already in the unblocking position when the CPU 45 judges the light volume insufficient, the first light blocking blade 57a is displaced from the blocking position toward the unblocking position and stopped at a position where the CPU 45 judges by the luminance information that the light volume gets proper.

As described so far, in the ordinary inspection mode, the illumination light is mostly projected from the second illumination system L2 using the second fiber bundle with large numerical aperture. If the light volume of the illumination light from the second illumination system L2 alone is insufficient for the ordinary inspection, the illumination light from the first illumination system L1 is added to gain a sufficient light volume.

In the ordinary inspection mode, the endoscopic images are acquired at a low image magnification to make screening for detecting and identifying suspected site of lesions. If necessary, the foot pedals 15 may be operated to change the image magnification.

When some suspected site of lesions is detected, the pedal 15a is operated to increase the image magnification. In response to the operation on the pedal 15a, the CPU 45 drives the zooming mechanism 41 to move the zoom lens 37b toward the telephoto side, increasing the image magnification. By setting the inspection window 20 closer to the suspected site, enlarged endoscopic images of the suspected site will be displayed on the monitor 14.

Meanwhile, when the focal length of the imaging optical system 37 gets over a middle focal length with the movement of the zoom lens 37b toward the telephoto side, the CPU 45 is switched to the close-up inspection mode. The focal length of the imaging optical system 37 may for example be measured by the driven amount of the zooming mechanism 41.

In the close-up inspection mode, the CPU 45 initially controls the second control unit 58 to move the second light blocking blade 58a into the blocking position to block the illumination light from entering the second entrance zone 52a, so that the target site will be illuminated only with the illumination light from the first illumination system L1. Next, the CPU 45 detects by the luminance information whether the light volume is excessive or sufficient. If the light volume of the illumination light from the first illumination system L1 is excessive or insufficient, the CPU 45 controls the first control unit 57 to adjust the inserted amount of the first light blocking blade 57a into the optical path to get a proper light volume. If the light volume is insufficient while the first light blocking blade 57a is completely in the unblocking position, the light volume may be boosted for example by increasing the gain of the AGC in the AFE 39.

Thus, in the close-up inspection mode, the target site is illuminated only with the illumination light from the first illumination system L1, in which the blue light component is less attenuated, and the illumination light from the second illumination system L2 having lots of long-wavelength light components is not projected toward the target site. Therefore, enlarged images displayed on the monitor 14 will clearly show the superficial blood vessels, which is helpful for making an exact diagnosis.

When the pedal 15b is operated in the close-up inspection mode to make the focal length of the imaging optical system 37 less than the middle focal length, the CPU 45 switches back to the ordinary inspection mode. Then, as described above, the target site is mainly illuminated with the illumination light from the second illumination system L2 in the ordinary inspection mode, and the illumination light from the first illumination system L1 may be additionally used to control the light volume.

Figure 7A:
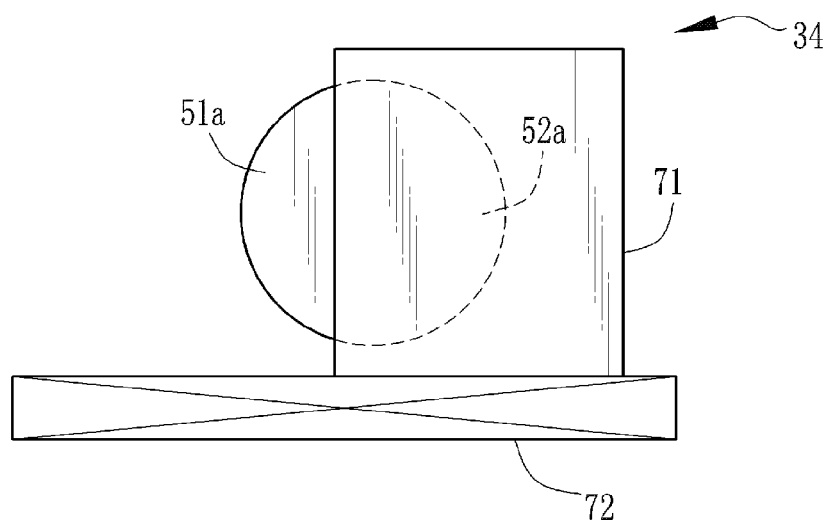
FIGS. 7A and 7B are explanatory diagrams illustrating the operation of a light volume control mechanism using a single blocking blade.
Figure 7B:
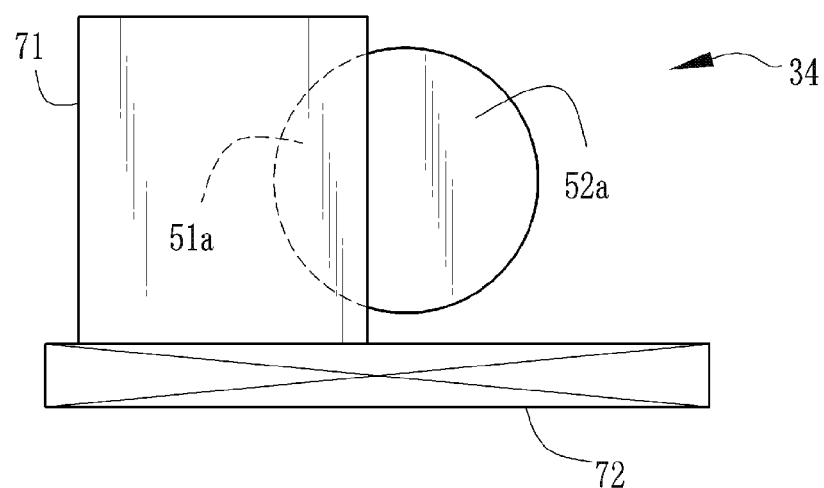

Referring to FIG. 7, a light volume control mechanism in accordance with another embodiment may include a single light blocking blade 71, which may be driven by an actuator 72 to move in an orthogonal direction to a border line between the entrance zones 51a and 52a. In the close-up inspection mode, the light blocking blade 71 is initially set in a terminal position as shown in FIG. 7A, where the light blocking blade 71 lets the illumination light from the light source fall in the entire area of the first entrance zone 51a while blocking the illumination light from the second entrance zone 52a. From this terminal position, the light blocking blade 71 may be moved in a direction to cover the first entrance zone 51a. Thus, the light blocking blade 71 may control the volume of light entering the first entrance zone 51a while blocking the illumination light from the second entrance zone 52a. On the other hand, in the ordinary inspection mode, the light blocking blade 71 is initially set at a home position as shown in FIG. 7B, letting the illumination light enter the entire area of the second entrance zone 52a, and blocking the illumination light from the first entrance zone 51a. From this home position, the light blocking blade 71 may be moved in opposite directions to control the light volume projected toward the target site.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

What is claimed is:

1. An endoscope system comprising:
   an imaging device having a varifocal imaging optical system mounted in a distal end of an endoscope, the distal end being inserted into a test subject to capture images of a target site inside the test subject through the imaging device;
   a light source for emitting illumination light;
   a light guide for conducting the illumination light from the light source to the distal end of the endoscope to project the illumination light toward the target site, the light guide comprising a first fiber bundle consisting of optical fibers of a first numerical aperture and a second fiber bundle consisting of optical fibers of a second numerical aperture larger than the first numerical aperture, the first and second light bundles having respective inlet ends for entry of the illumination light from the light source and respective outlet ends placed in the distal end of the endoscope;
   a light volume control mechanism switchable between a second fiber bundle unblocking position allowing the illumination light from the light source to enter the second fiber bundle and a second fiber bundle blocking position blocking the illumination light from entering the second fiber bundle; and
   a control device for controlling the light volume control mechanism, the control device setting the light volume control mechanism in the second fiber bundle blocking position in a close-up inspection mode, wherein the imaging optical system has a focal length equal to or longer than a predetermined value, to project the illumination light only from the first fiber bundle in the close-up inspection mode.

2. The endoscope system as recited in claim 1, wherein the first and second fiber bundles are configured such that the illumination light projected from the first fiber bundle has a smaller volume than the illumination light projected from the second fiber bundle while the light volume control mechanism is in the second fiber bundle unblocking position.

3. The endoscope system as recited in claim 2, wherein the first fiber bundle consists of a smaller number of optical fibers than the second fiber bundle.

4. The endoscope system as recited in claim 1, wherein an inspection window for capturing images through the imaging device, a first lighting window for projecting the illumination light from the first fiber bundle, and a second lighting window for projecting the illumination light from the second fiber bundle are provided in an end face of the distal end, the first lighting window being located closer to the inspection window than the second lighting window to the inspection window.

5. The endoscope system as recited in claim 1, wherein the inlet ends of the first and second fiber bundles are united together and partitioned into respective zones, while the outlet ends of the first and second fiber bundles constitute two branches of the light guide.

6. The endoscope system as recited in claim 1, wherein the first numerical aperture is less than 0.5, and the second numerical aperture is not less than 0.5.

7. The endoscope system as recited in claim 1, wherein the control device sets the light volume control mechanism in the second fiber bundle unblocking position in an ordinary inspection mode, wherein the imaging optical system has a focal length shorter than the predetermined value, to project the illumination light from the second fiber bundle toward the target site in the ordinary inspection mode.

8. The endoscope system as recited in claim 7, wherein the light volume control mechanism is switchable between a first fiber bundle unblocking position allowing the illumination light from the light source to enter the first fiber bundle and a first fiber bundle blocking position blocking the illumination light from entering the first fiber bundle, wherein
    the control device sets the light volume control mechanism in the first fiber bundle blocking position in the ordinary inspection mode.

9. The endoscope system as recited in claim 8, wherein the light volume control mechanism may individually adjust the volume of light entering the first fiber bundle from the light source and the volume of light entering the second fiber bundle from the light source, and
    the control device controls the light volume control mechanism in the ordinary inspection mode to keep the first fiber bundle blocking position and adjust the volume of light entering the second fiber bundle when the volume of light projected toward the target site is excessive, or retreat from the first fiber bundle blocking position to adjust the volume of light entering the first fiber bundle when the volume of light projected only from the second fiber bundle is insufficient.

10. The endoscope system as recited in claim 7, wherein the light volume control mechanism may individually adjust the volume of light entering the first fiber bundle from the light source and the volume of light entering the second fiber bundle from the light source, and
    the control device controls the light volume control mechanism in the close-up inspection mode to keep the second fiber bundle blocking position and adjust the volume of light entering the first fiber bundle when the volume of light projected toward the target site is excessive or insufficient.

* * * * *